United States Patent
Kim et al.

(10) Patent No.: US 10,364,328 B2
(45) Date of Patent: Jul. 30, 2019

(54) METHOD FOR PRETREATING LIGNOCELLULOSE BY USING ACID-BASE MIXTURE CATALYST

(71) Applicant: Korea University Research and Business Foundation, Seoul (KR)

(72) Inventors: Kyoung Heon Kim, Seoul (KR); Young Hoon Jung, Seoul (KR)

(73) Assignee: Korea University Research and Business Foundation, Seoul (KR)

(*) Notice: Subject to any disclaimer, the term of this patent is extended or adjusted under 35 U.S.C. 154(b) by 58 days.

(21) Appl. No.: 15/306,533

(22) PCT Filed: Apr. 27, 2015

(86) PCT No.: PCT/KR2015/004158
§ 371 (c)(1),
(2) Date: Oct. 25, 2016

(87) PCT Pub. No.: WO2015/163738
PCT Pub. Date: Oct. 29, 2015

(65) Prior Publication Data
US 2017/0044329 A1    Feb. 16, 2017

(30) Foreign Application Priority Data
Apr. 25, 2014 (KR) ........................ 10-2014-0050186

(51) Int. Cl.
C08B 1/00 (2006.01)
C08H 8/00 (2010.01)
C12P 7/10 (2006.01)

(52) U.S. Cl.
CPC ................ C08H 8/00 (2013.01); C08B 1/00 (2013.01); C12P 7/10 (2013.01); C12P 2201/00 (2013.01); Y02E 50/16 (2013.01); Y02E 50/17 (2013.01)

(58) Field of Classification Search
None
See application file for complete search history.

(56) References Cited

U.S. PATENT DOCUMENTS
8,123,864 B2    2/2012    Christensen et al.

FOREIGN PATENT DOCUMENTS

| KR | 101238932 A | 3/2013 |
| KR | 10-2013-0100039-MT | * 9/2013 |
| KR | 1020140012253 A | 2/2014 |
| KR | 101621126 A | 5/2016 |

OTHER PUBLICATIONS

Koo et al. (Characterization of by-products from organosolv pretreatments of yellow poplar wood (*Liriodendron tulipifera*) in the presence of acid and alkali catalysts. Journal of Industrial and Engineering Chemistry, (2011), 17: 18-24).*
Noda et al. Sequential combination of acid and base for conversion of cellulose., Energy Fuels (2012), 26: 2376-2385.*
Jung et al., "Dilute acid pretreatment of lignocellulose for whole slurry ethanol fermentation," Bioresource Technology (2013); 132:109-114.
Lynd et al., "Biocommodity Engineering," Biotechnol. Prog. (1999); 15:777-793.
Shi et al., "One-pot ionic liquid pretreatment and saccharification of switchgrass," Green Chem (2013); 15:2579-2589.
Sluiter et al., "Determination of Structural Carbohydrates and Lignin in Biomass," Laboratory Analytical Procedure (LAP) (Issue Date: Apr. 2008/Revision Date: Aug. 3, 2012); pp. 1-18.

* cited by examiner

Primary Examiner — Iqbal H Chowdhury
(74) Attorney, Agent, or Firm — Fox Rothschild LLP

(57) ABSTRACT

The present invention relates to a method for pretreating lignocellulose by using an acid-base mixture catalyst. The method pretreats lignocellulose, by using a mixture catalyst of an acid and a base, so as not to pass through additional neutralization steps, and carries out pretreatment and simultaneous saccharification and fermentation through an identical single reactor process, thereby having an effect of producing ethanol in an excellent production yield from lignocellulosic biomass while simplifying the total process and reducing equipment costs and total processing costs.

3 Claims, 15 Drawing Sheets

METHOD FOR PRETREATING LIGNOCELLULOSE BY USING ACID-BASE MIXTURE CATALYST

CROSS-REFERENCE TO RELATED APPLICATIONS

This application is the U.S. National Phase of International Patent Application No. PCT/KR2015/004158, filed Apr. 27, 2015, which claims priority to Korea Patent Application No. 10-2014-0050186, filed Apr. 25, 2014, the disclosures of which are incorporated herein by reference.

BACKGROUND

1. Field of the Invention

The present invention relates to a method for pretreating cellulosic biomass by using a mixture catalyst of an acid and a base in pretreatment for pretreatment, saccharification, and fermentation of lignocellulose in just one reactor (one-pot process).

2. Discussion of Related Art

In order to produce a biofuel from lignocellulose, recalcitrance of lignocellulose itself should be alleviated through suitable physicochemical pretreatment. However, since a major pretreatment process is performed at a high temperature and a pH in a range of a strong acid or a strong base, degradative products (furfural, etc.) are generated, which cause not only sugar loss but also the inhibition of a yeast fermentation process.

Meanwhile, a process for producing a biofuel from lignocellulose mainly progresses through pretreatment, solid/liquid separation, solids washing, liquid detoxification, liquid neutralization, enzymatic hydrolysis, and ethanol fermentation processes. Among these, unit processes for removal of inhibitory compounds such as solid/liquid separation, solids washing, liquid detoxification, and liquid neutralization make total operating costs significantly increase. Therefore, there are needs for the development of a strain which is tolerable to the inhibitor, or of a new process in which an inhibitor is not produced.

As part of such efforts, consolidate bioprocessing (CBP) in which enzyme production and fermentation are performed in a single step using a genetically modified microorganism was suggested (Lynd et at., *Biotechnol. Prog.*, 1999, 15, pp. 777-793), but has not realized yet. Also, whole slurry fermentation in which saccharification and fermentation are performed without a solid/liquid separation process was suggested (Jung et at., *Bioresour. Technol.*, 2013, 132, pp. 109-114), but was again found inconvenient to additionally remove inhibitors using activated carbon, etc. In addition, a method for combining pretreatment with hydrolysis using an ionic liquid was suggested as well, but was found inconvenient in that an ionic liquid should be separated and recovered after pretreatment due to costs and toxicity thereof, and as part of some other integrated process, a simultaneous saccharification and fermentation process itself is impossible (Shi et al., Green Chem., 2013, 15, pp. 2579-2589).

Therefore, the development of processing technology capable of simplifying the overall process, reducing total operating costs, and improving the production yield of ethanol is being demanded.

SUMMARY OF THE INVENTION

The main objective of the present invention is to provide a method for pretreating lignocellulose by using an acid-base mixture catalyst in pretreatment in order to obtain ethanol from lignocellulose by carrying out pretreatment, saccharification, and fermentation process in one reactor.

Another object of the present invention is to provide a method for producing ethanol from lignocellulosic biomass by using the modified pretreatment method aforementioned.

For achieving the objects, the present invention provides a method for pretreating lignocellulosic biomass comprising, reacting an acid-base mixture catalyst having a pH value of 1 to 4 with lignocellulosic biomass.

The present invention also provides a method for producing ethanol from lignocellulosic biomass comprising, carrying out simultaneous saccharification and fermentation on a whole slurry obtained by pretreating the lignocellulosic biomass with an acid-base mixture catalyst having a pH value of 1 to 4.

The present invention is effective for increasing saccharification efficiency by pretreating lignocellulosic biomass with an acid-base mixture catalyst, and thereby improving the production yield of ethanol.

Also, the present invention is effective for simplifying the overall process and thereby significantly reducing total operating costs since pretreatment, enzymatic hydrolysis, saccharification, and fermentation process of lignocellulosic biomass are performed in one reactor, and additional steps such as milling of biomass, solid/liquid separation after pretreatment, separated solids washing, separated liquid detoxification, pH neutralization of a whole slurry and the like are not undergone.

BRIEF DESCRIPTION OF THE DRAWINGS

FIG. 4B shows enzymatic digestibility obtained through enzymatic hydrolysis after pretreatment of rice straw with mixture catalyst of HCl/NaOH at various total concentration, FIG. 4C shows enzymatic digestibility obtained through enzymatic hydrolysis after pretreatment of rice straw with mixture catalyst of HCl/KOH at various mixing ratio, and FIG. 4D shows enzymatic digestibility obtained through enzymatic hydrolysis after pretreatment of rice straw with mixture catalyst of HCl/NH$_3$ at various mixing ratio.

FIG. 5B shows enzymatic digestibility obtained through enzymatic hydrolysis after pretreatment of rice straw with mixture catalyst of H$_2$SO$_4$/KOH at various mixing ratio, and FIG. 5C shows enzymatic digestibility obtained through enzymatic hydrolysis after pretreatment of rice straw with mixture catalyst of H$_2$SO$_4$/NH$_3$ at various mixing ratio.

FIG. 6B shows enzymatic digestibility obtained through enzymatic hydrolysis after pretreatment of rice straw with mixture catalyst of $CH_3COOH/KOH$ at various mixing ratio, and FIG. 6C shows enzymatic digestibility obtained through enzymatic hydrolysis after pretreatment of rice straw with mixture catalyst of $CH_3COOH/NH_3$ at various mixing ratio.

DETAILED DESCRIPTION OF EXEMPLARY EMBODIMENTS

Figure 1:
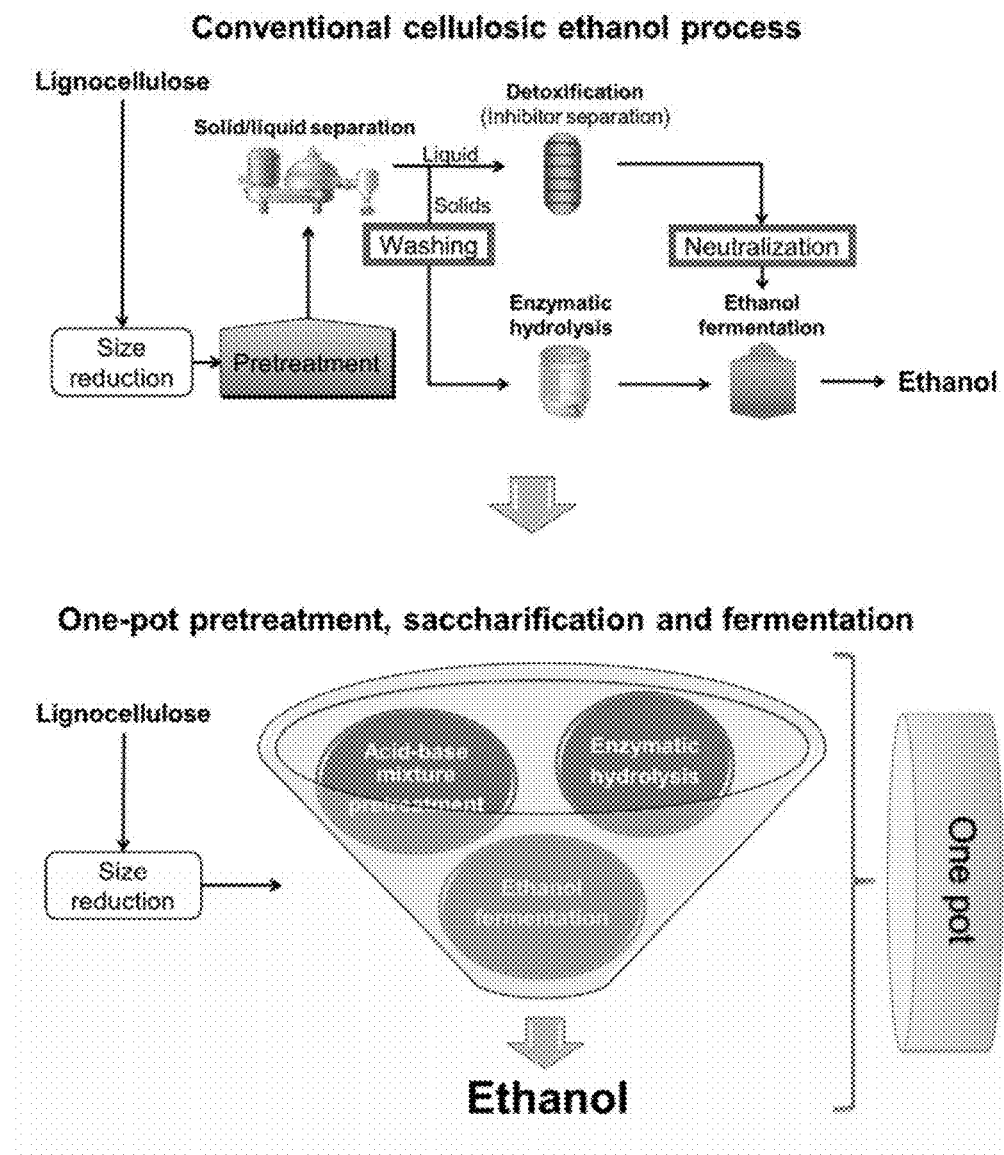
FIG. 1 is a schematic view illustrating a conventional process for producing ethanol from lignocellulosic biomass and a process according to the present invention.

Hereinafter, the composition of the present invention will be described in detail.

The present invention relates to a method for pretreating lignocellulosic biomass comprising, reacting an acid-base mixture catalyst having a pH value of 1 to 4 with lignocellulosic biomass.

The acid-base mixture catalyst is prepared in an acidic pH range by mixing an acid and base at an appropriate molar ratio and is used for reaction with lignocellulosic biomass.

A type of the acid used for the acid-base mixture catalyst may include sulfuric acid, maleic acid, hydrochloric acid, nitric acid, phosphoric acid, carbonic acid, formic acid, acetic acid, hydrofluoric acid, oxalic acid, or citric acid, etc., but is not limited thereto.

A type of the base used for the acid-base mixture catalyst may include sodium hydroxide, potassium hydroxide, calcium hydroxide, barium hydroxide, ammonium hydroxide, calcium carbonate, potassium carbonate, or ammonia, etc., but is not limited thereto.

The acid-base mixture catalyst may be used by ensuring that a total concentration becomes 0.01 to 1 M by mixing an acid and a base at a molar ratio upon pretreatment of lignocellulosic biomass in order to minimize the generation of an inhibitor which impedes saccharification and fermentation after the pretreatment of lignocellulosic biomass. By causing a mixing ratio of the acid and base to become an acidic condition, that is, a condition of pH 1 to 4, the pH range is similar to that when pretreatment with an existing acid catalyst, but, according to one embodiment of the present invention, it is confirmed that, as in FIGS. 2, 7, and 10, a saccharification yield when pretreatment with the mixture catalyst of an acid and a base is higher than when pretreatment with only an acid catalyst. Through such a result, it is thought to lose its own catalyst characteristics which an acid or a base has when an acid and a base are mixed, but as seen in the present invention, when a specific mixing ratio and concentration are provided, it was found that the mixture catalyst of an acid and a base not only improves a saccharification yield in a range of pH 1 to 4 but also does not undergo additional neutralization steps using a base because a pH within a whole slurry after pretreatment corresponds to a weak acidic range.

In addition, the acid-base mixture catalyst is stable at normal temperature, and therefore stability as a catalyst for pretreatment is ensured. According to one embodiment, it was found that when pretreatment is performed after an acid-base mixture catalyst is incubated at normal temperature for about 48 hours before pretreatment of sugarcane bagasse, a saccharification yield is not affected at all, and characteristics as a catalyst for pretreatment do not change.

According to one embodiment of the present invention, when the acid-base mixture catalyst is used, the generation of an inhibitor such as acetic acid, furfural, hydroxymethyl furfural, and the like may be reduced.

The acid-base mixture catalyst may be treated in an amount of 4 to 20% (w/v) by 1 part by weight of lignocellulosic biomass. When an amount of solids loading is more than 20%, it is difficult to transfer material and heat such that saccharification efficiency may decrease, and when an amount of solids loading is less than 4%, a concentration of a final product may decrease due to a low loading amount.

Lignocellulosic biomass such as rice straw, giant miscanthus, sugarcane bagasse, corn byproducts, switchgrass, poplar, oil palm byproducts, oak, an energy crop and the like may be used as lignocellulosic biomass for pretreatment, but is not limited thereto. In addition, such pretreatment may have a similar effect on cellulosic biomass or industrial waste composed of cellulose, hemicellulose, lignin and the like.

According to one embodiment of the present invention, rice straw, oil palm frond, sugarcane bagasse and the like may be used as lignocellulosic biomass, and the rice straw, oil palm fronds, or sugarcane bagasse may be dried and ground to a size of a few mm or less using a rotary-type mill, but is not limited thereto.

The pretreatment reaction may be performed at temperatures of 100 to 200° C. for 60 seconds to 2 hours, and have an effect of simplifying the overall process and reducing production costs because pH of reactant corresponds to a weak acid by using the mixture catalyst of an acid and a base, and thus a neutralization process which is performed before a saccharification and fermentation process does not need to be additionally carried out.

The present invention also relates to a method for preparing ethanol from lignocellulosic biomass comprising, carrying out simultaneous saccharification and fermentation on a whole slurry obtained by pretreating lignocellulosic biomass with an acid-base mixture catalyst having a pH value of 1 to 4.

Generally, chemical pretreatment and a saccharification process using enzymes cost the most when using biomass which is renewable forestry waste. Conventional technologies placed an emphasis on an increase in yield through these, and also, there was a disadvantage of substantially increasing total operating costs because the overall process includes existing unit processes, for example, milling of biomass, solid/liquid separation after pretreatment, separated solids washing, separated liquid detoxification, pH neutralization of a whole slurry and the like, all of which are complicated processes.

In contrast, the present invention has differentiated features from the conventional technologies in that first, an acid-base mixture catalyst is used in pretreatment, and second, additional neutralization steps are not undergone, and finally, the overall process is performed in one reactor.

First, in the case of using an acid-base mixture catalyst in pretreatment, conventionally a pretreatment step using acid or base is separately performed due to inherent properties of an acid and base catalyst, but in the present invention, an acid and a base are mixed at an appropriate molar ratio, an acid-base mixture catalyst is used under an acidic condition of pH 1 to 4 in pretreatment, and thus, although an absolute amount of a used catalyst decreases, a whole saccharification/fermentation yield may be maintained without change. That is, there is an advantage of increasing the output amount of products based on the input amount of biomass.

Next, additional neutralization steps are not undergone. A neutralization step is absolutely necessary for a subsequent saccharification and fermentation process since existing catalysts are applied in a strong acidic or strong basic range of a pH, and existing catalysts cause not only sugar loss but also the inhibition of a yeast fermentation process by generating glycolysis products with the addition of additional bases or acids. Furthermore, such addition of bases or acids makes a whole process economically worse in terms of costs for the addition or costs for removing a produced salt.

In contrast, in the present invention, an acid-base mixture catalyst (ranging from pH 1 to pH 4) is used in pretreatment and then it is confirmed that a pH of a whole slurry is approximately in a weak acidic range, and as a result, additional neutralizing agents do not need to be added besides a buffer for cultivating microorganisms. Also, since the whole slurry obtained through pretreatment is used for producing products, an existing solid/liquid separation process, solids washing, a liquid detoxification process, a liquid neutralization process may be omitted, which causes costs to be considerably reduced in the biofuel and biorefinery industry.

Finally, since simultaneous saccharification and fermentation process on the whole slurry obtained by pretreatment is performed in one reactor, costs required for process equipment may remarkably decrease.

A method for preparing ethanol from lignocellulosic biomass of the present invention includes performing simultaneous saccharification and fermentation on the whole slurry of lignocellulosic biomass pretreated with a mixture catalyst of an acid and a base to prepare ethanol according to a schematic view illustrating a process in FIG. 1.

Since a pH of the whole slurry is in a weak acidic range and thus additional neutralization steps do not need to be undergone before saccharification, saccharification and fermentation on the whole slurry may be directly performed.

Generally, a saccharification step and a fermentation step may be performed through a separate hydrolysis and fermentation (SHF) process in which saccharification and fermentation are carried out in individual reactors, or through a simultaneous saccharification and fermentation (SSF) process in which saccharification and fermentation are carried out in one reactor at the same time. In the SSF process, since yeast may remove glucose through a fermentation step and accumulation of sugars in the reactor may be minimized as soon as glucose is produced, inhibition of a final product shown in the SHF process may be prevented and enzymatic hydrolysis may be improved. Also, equipment costs may be reduced, costs may be reduced by a low input amount of enzymes, and a contamination problem may decrease due to ethanol present in the reactor. Furthermore, since simultaneous saccharification and fermentation could be directly carried out in the reactor in which a pretreatment step is performed, one-pot process of the present invention may be realized. Therefore, the present invention uses simultaneous saccharification and fermentation.

Enzymes used in the saccharification may include cellulase, α-amylase, glucoamylase, endoglucanase, xylanase, β-glucosidase, α-agarase, β-agarase I, β-agarase II, β-galactosidase, neoagarobiose hydrolase, neoagarotetraose hydrolase, neoagarohexaose hydrolase, α-neoagarobiose hydrolase, or mixtures or composites thereof, etc., but is not limited thereto.

In addition, microorganisms used in fermentation may include, for example, *Saccharomyces cerevisiae, Klebsiella oxytoca* P2, *Brettanomyces curstersii, Saccharomyces uvzrun, Candida brassicae. Sarcina ventriculi, Zymomonas mobilis, Kluyveromyces marxianus* IMB3, *Clostridium acetobutylicum, Clostridium beijerinckii, Kluyveromyces fragilis, Brettanomyces custersii, Clostriduim aurantibutylicum,* and *Clostridium tetanomorphum,* etc., but the present invention is not limited thereto.

Conditions for performing the simultaneous saccharification and fermentation are not particularly limited, and the reaction may be performed while stirring for example, in a concentration of initial glucose ranging 2 to 30% (w/v) at temperatures of 25 to 40° C. at a pH of 4.0 to 8.0 at a speed of 50 to 250 rpm.

If necessary, those skilled in the art can perform other additional steps and/or processes, for example, a purification step in which a fermented liquid obtained by the simultaneous saccharification and fermentation step is purified according to a method known in the art.

Hereinafter, the present invention will be described in detail according to exemplary embodiments. However, the following exemplary embodiments are merely presented to exemplify the present invention, and the content of the present invention is not limited to the following exemplary embodiments.

EXAMPLE 1

Effects of Saccharification or Simultaneous Saccharification and Fermentation in Accordance with Pretreatment of Rice Straw Rice straw was used as a representative example of lignocellulose, and glucose and the production of ethanol through a fermentation process were confirmed as representative examples of products.

First, in order to confirm effects of pretreatment with an acid-base mixture catalyst, a mixture catalyst mixed based on types of an acid and a base was prepared, wherein a mixing ratio (a pH condition) and concentration of the mixture catalyst were optimized, and in order to confirm reaction mechanisms of the acid-base mixture catalyst and a difference with only an existing acid or base catalyst, biomass composition and enzymatic digestibility were compared. In addition, enzymatic accessibility of biomass treated with the acid-base mixture catalyst was confirmed. Finally, saccharification and fermentation were performed in a reactor including a whole slurry without additional processes such as solid/liquid separation, separated solids washing, separated liquid detoxification, pH neutralization of a whole slurry and the like on the whole slurry of biomass pretreated with the acid-base mixture catalyst, and the yield of ethanol was confirmed (referring to FIG. 1).

Rice straw was harvested from Yeonggwang (South Korea), washed, dried, and then cut into a range of 90 to 1000 μm using a high speed rotary cutter (MF 10 commercially available from IKA, Staufen, Germany).

Hydrochloric acid, sulfuric acid, acetic acid, sodium hydroxide, potassium hydroxide, ammonia, sodium chloride and the like were mixed at an appropriate ratio, were diluted to a desired concentration, and were used in a pretreatment step. While 2 g of dried rice straw were soaked in 20 mL of a catalyst in a 100 mL container and then was reacted in a mini thermal reactor at 190° C. for 2 minutes, tests were performed based on various changes in a mixing ratio of an acid and a base, a concentration of a catalyst and the like, wherein a pH was under an acidic condition, a neutral condition, an alkaline condition and a concentration was in a range of 0 to 1 M.

After completion of pretreatment, an insoluble solid was recovered by filtering a pretreated slurry using a filter cloth (pore size: 22 to 25 μm, Calbiochem, La Jolla, Calif., USA) for composition analysis. Afterward, the pretreated insoluble solid was washed with about 1 L of distilled water until a pH value of a washing solution becomes 6 to 7, and then a washed solid was dried in a vacuum drying oven for 3 days or more at 45° C.

Composition analysis of pretreated biomass (a whole slurry) or untreated biomass was measured using a NREL method (Sluiter A et at., *Laboratory Analytical Procedure: Determination of Structural Carbohydrates and Lignin in Biomass*, National Renewable Energy Laboratory, Golden, Colo. 2008) for carbohydrates and acid-insoluble lignin. Moisture content in biomass was measured on the basis of the NREL method. In compositional analysis of carbohydrates, sugar content and enzymatic digestibility are determined using an ion exchange column (HPX-87P; commercially available from Biorad, Hercules, Calif.) including $Pb^{2+}$, and sugar detection was performed through a refractive index detector. For measuring inhibitors such as acetic acid, furfural, hydroxymethyl furfural (HMF) and the like, a column (HPX-87H; commercially available from Biorad, Hercules, Calif.) including $H^+$ was used, and also the measurement was performed through a refractive index detector. All analyses were repeated 3 times.

For measuring enzymatic digestibility, the insoluble solids washed after pretreatment of rice straw or untreated rice straw itself was subjected to enzymatic hydrolysis using Accellerase 1000 (commercially available from Genencor, Rochester, N.Y.) which is in the same added amount as 7 to 60 FPU of cellulase/g-glucan. A reaction mixture including biomass washed after pretreatment with 1% glucan was stirred in a 0.05 M sodium citrate buffer solution (pH 4.8) at 50° C. at 200 rpm, while being cultivated in a shaking incubator. Enzymatic digestibility represented by the theoretical maximum yield of glucose was determined as a ratio of glucose (g) produced through hydrolysis to the total glucose (g) within initial biomass used in enzymatic hydrolysis.

For investigating fermentation capability of pretreated biomass, a simultaneous saccharification and fermentation test was performed. A fermentation medium was composed of a 0.05 M citric acid buffer solution (pH 4.8), a 1% (w/v) yeast extract and 2% (w/v) peptone. A untreated substrate or a pretreated and washed substrate was added by a final glucan concentration of 3% (w/v) in a total 100 mL of a medium and a whole slurry of bundle pretreated and neutralized was added using a final substrate concentration of 6% (w/v) in a 250 mL-flask with a needle-pierced silicone stopper for a micro-aerobic condition and venting $CO_2$ produced during fermentation. After sterilization, fermentation was performed using pre-grown *Saccharomyces cerevisiae* $D_5A$ (ATCC 200062) while stirring at 38° C. at 170 rpm.

For analyzing the accessibility of cellulase with respect to cellulose of pretreated rice straw, binding capacity was measured using Type A surface-binding protein3 (CtCBD3) derived from *Clostridium thermocellum*. 5 mg of untreated or pretreated biomass was incubated with an excess amount of BSA protein or CtCBD3 and a 50 mM phosphate buffer solution (pH 7) and then supernatant and pellet were separated by centrifugation after 3.5 hours, and an amount of unbound protein was measured by the Bradford method.

TABLE 1

Composition analysis of rice straw pretreated by using different catalysts

| | untreated | acid-base mixture catalyst (0.04M HCl + 0.01M NaOH) | HCl (0.04M) | NaOH (0.01M) | NaCl (0.01M) |
|---|---|---|---|---|---|
| Component from insoluble solids (g/100 g dry rice straws before pretreatment) | | | | | |
| insoluble solids recovery yield | — | 55.6 ± 2.5 | 55.9 ± 2.6 | 75.5 ± 0.8 | 85.0 ± 3.9 |
| glucan | 35.8 ± 1.5 | 32.3 ± 0.6 | 30.9 ± 0.3 | 33.7 ± 0.0 | 33.1 ± 0.4 |
| xylan | 10.5 ± 1.4 | 3.9 ± 0.5 | 2.9 ± 0.2 | 10.7 ± 0.2 | 10.5 ± 0.4 |
| galactan | 0.3 ± 0.3 | 1.5 ± 1.4 | 2.2 ± 0.0 | 2.9 ± 0.0 | 3.4 ± 0.0 |
| arabinan | 3.1 ± 0.5 | 1.8 ± 0.0 | 1.7 ± 0.0 | 2.3 ± 0.0 | 2.6 ± 0.0 |
| lignin | 18.2 ± 1.3 | 11.0 ± 0.3 | 10.7 ± 0.0 | 10.8 ± 0.3 | 12.2 ± 0.2 |
| Component from dissolved solids (g/100 g rice straw before pretreatment) | | | | | |
| glucose | — | 4.9 ± 0.2 | 6.1 ± 0.0 | 0.5 ± 0.0 | 1.5 ± 0.0 |
| hemicellulose monomer $^c$ | — | 10.2 ± 0.1 | 14.9 ± 0.1 | 0.5 ± 0.0 | 1.3 ± 0.1 |

TABLE 1-continued

Composition analysis of rice straw pretreated by using different catalysts

|  | untreated | acid-base mixture catalyst (0.04M HCl + 0.01M NaOH) | HCl (0.04M) | NaOH (0.01M) | NaCl (0.01M) |
|---|---|---|---|---|---|
| acetic acid | — | 1.5 ± 0.0 | 2.0 ± 0.1 | 1.6 ± 0.0 | 0.3 ± 0.1 |
| HMF | — | 0.4 ± 0.0 | 0.5 ± 0.0 | 0.0 ± 0.0 | 0.0 ± 0.0 |
| furfural | — | 0.6 ± 0.0 | 0.7 ± 0.0 | 0.0 ± 0.0 | 0.0 ± 0.0 |

Figure 2:
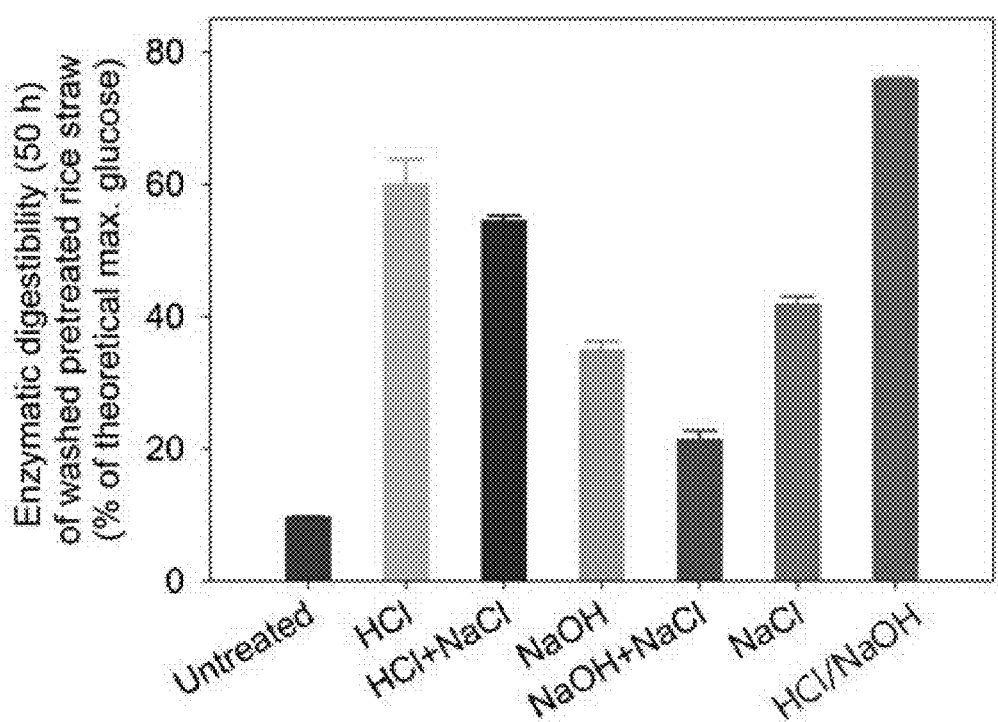
FIG. 2 shows effects of pretreatment of rice straw with an acid, a base, and an acid-base mixture catalyst, that is, 0.04 M HCl, 0.04 M HCl/0.01 M NaCl, 0.01 M NaOH, 0.01 M NaOH/0.01 M NaCl, 0.01 M NaCl, and 0.04 M HCl/0.01 M NaOH.

[a] Pretreatment conditions: performed in a mini thermal reactor at 190° C. for 2 minutes, and solids loading in an amount of 10% (w/v)
[b] Experimental data is expressed as means ± standard deviations
[c] Hemicellulose monomer includes xylose, galactose, and arabinose in a liquid fraction thereof As shown in FIG. 2, after pretreatment with an acid, a base, or an acid-base mixture catalyst, the use of an acid-base mixture catalyst produces relatively excellent enzymatic digestibility.

Figure 3:
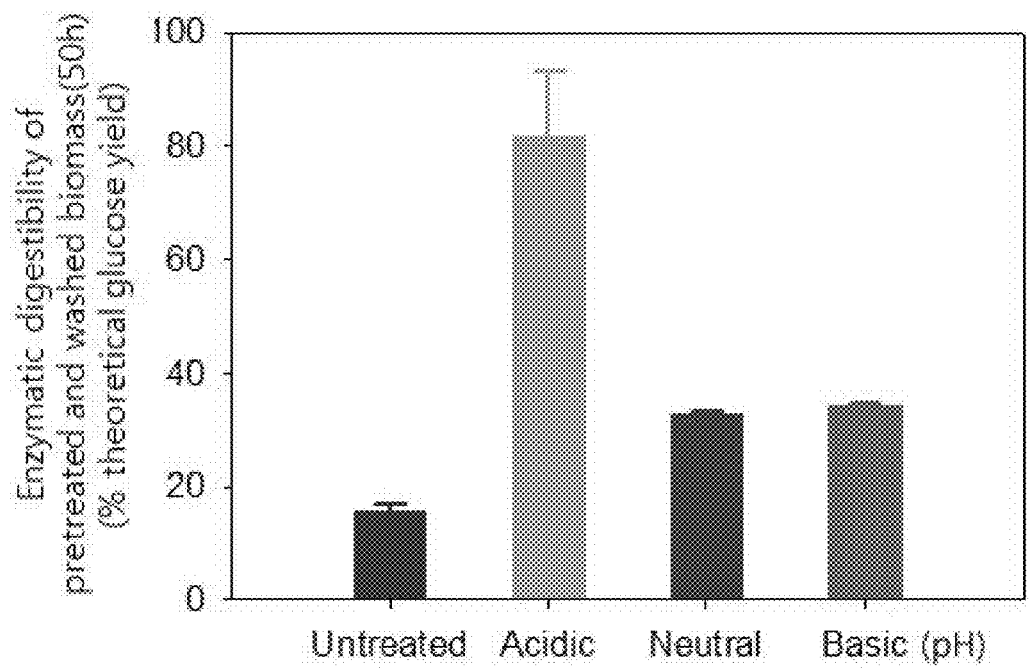
FIG. 3 shows enzymatic digestibility in a pH range and a total concentration of an acid-base mixture catalyst upon pretreatment of rice straw.
Figure 3:
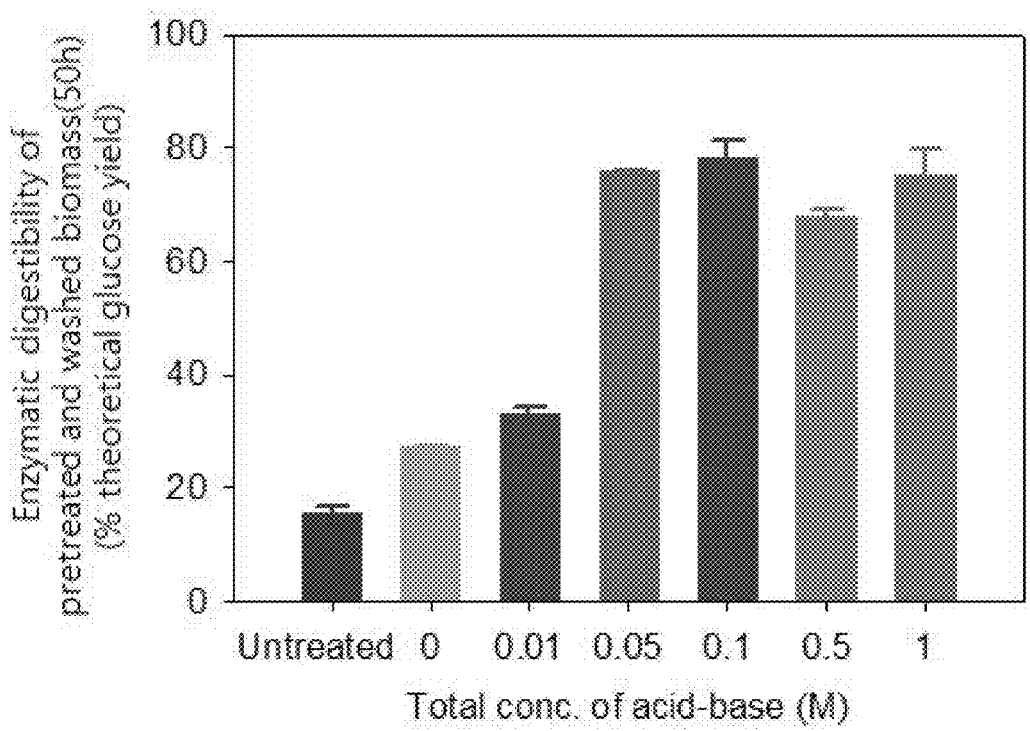

FIG. 3 shows enzymatic digestibility in a pH range and a total concentration of an acid-base mixture catalyst when pretreating rice straw, wherein a 10% (w/v) substrate was pretreated by loading in a mini thermal reactor at 190° C. for 2 minutes and then enzymatic hydrolysis was performed on biomass washed with distilled water, and stirring was performed with the addition of 15 FPU/g glucan at pH 4.8 at 50° C. at 200 rpm for 50 hours. In FIG. 3, an acidic condition refers to a case in which an acidic proportion is high within a mixture catalyst, a neutral condition refers to a case in which an acidic proportion is similar to a basic proportion, and a basic condition refers to a case in which a basic proportion is high, each of which means a pH range of about pH 1 to 4, 4 to 9, and 8 to 14, respectively. Also, in FIG. 3 a concentration "0" means treatment with water, which is also applicable to FIGS. 4 and 13.

This process results in confirming if the pretreatment was properly performed, wherein, in the case of pretreatment with the acid-base mixture catalyst, effects of pretreatment were improved under an acidic condition (range of pH 1 to 4 in which an acidic proportion is high), and the more a concentration of the mixture catalyst increased, the more effects of pretreatment were improved (FIG. 3B).

Figures 4A, 4B, 4C, 4D:
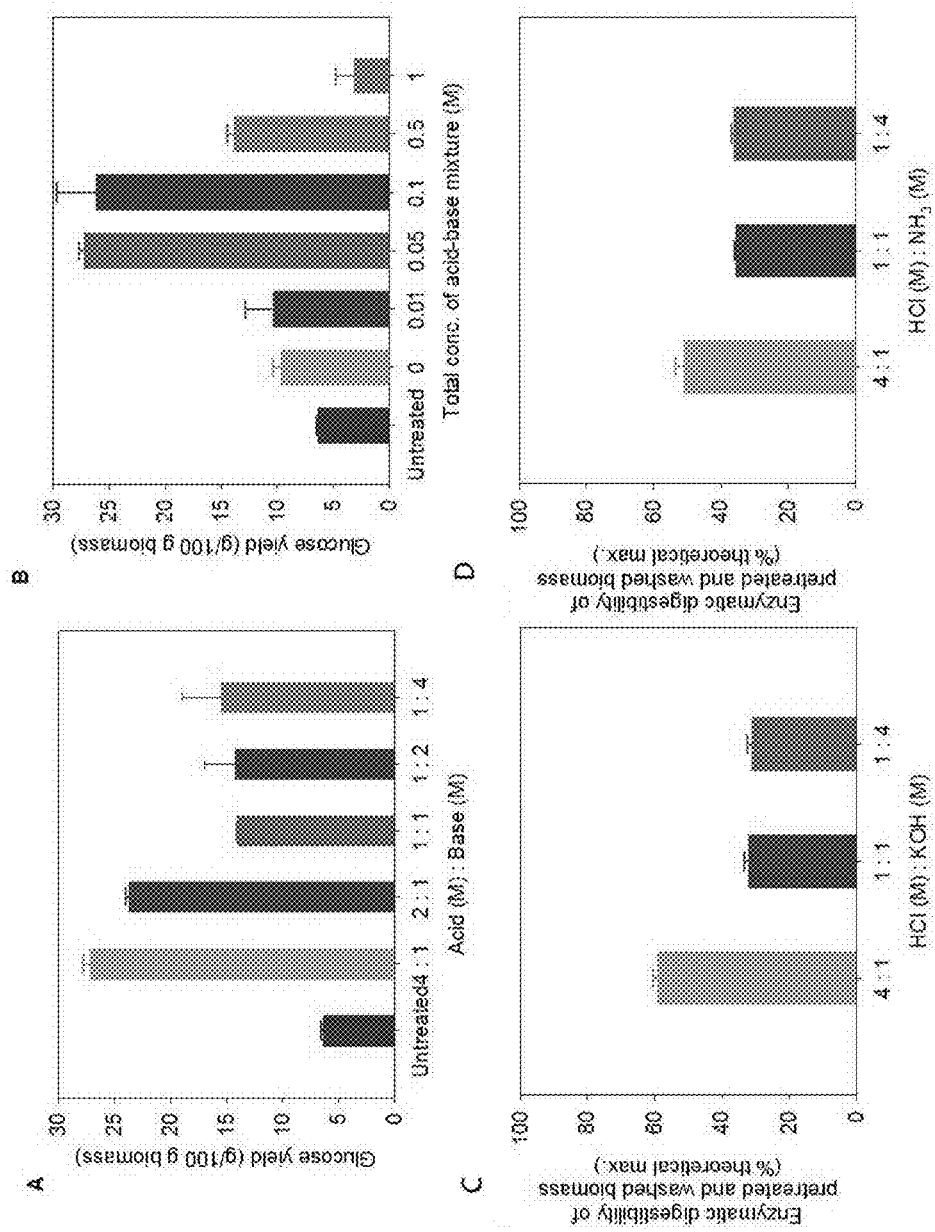
FIGS. 4A, 4B, 4C and 4D-FIG. 4A shows enzymatic digestibility obtained through enzymatic hydrolysis after pretreatment of rice straw with mixture catalyst of HCl/NaOH at various mixing ratio.
Figures 5A, 5B, 5C:
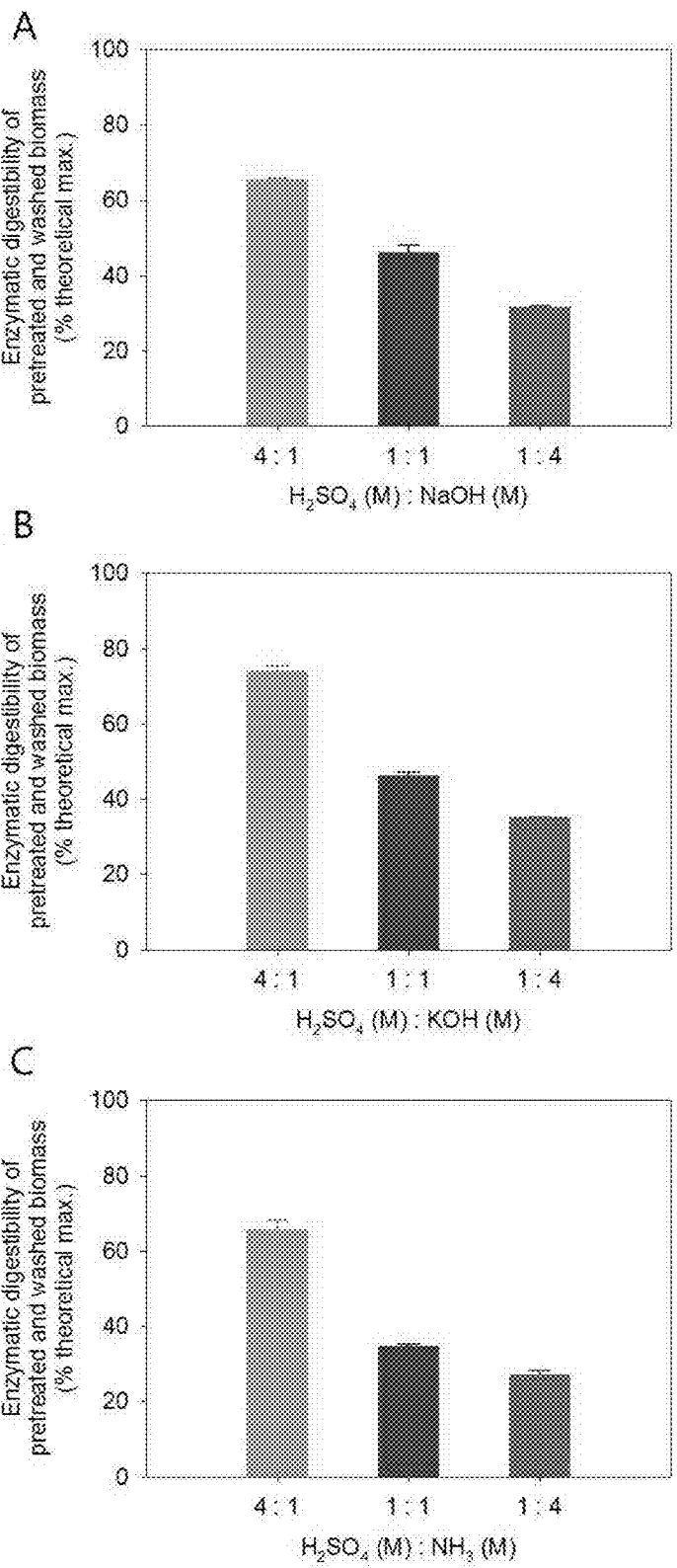
FIGS. 5A, 5B and 5C-FIG. 5A shows enzymatic digestibility obtained through enzymatic hydrolysis after pretreatment of rice straw with mixture catalyst of H$_2$SO$_4$/NaOH at various mixing ratio.
Figures 6A, 6B, 6C:
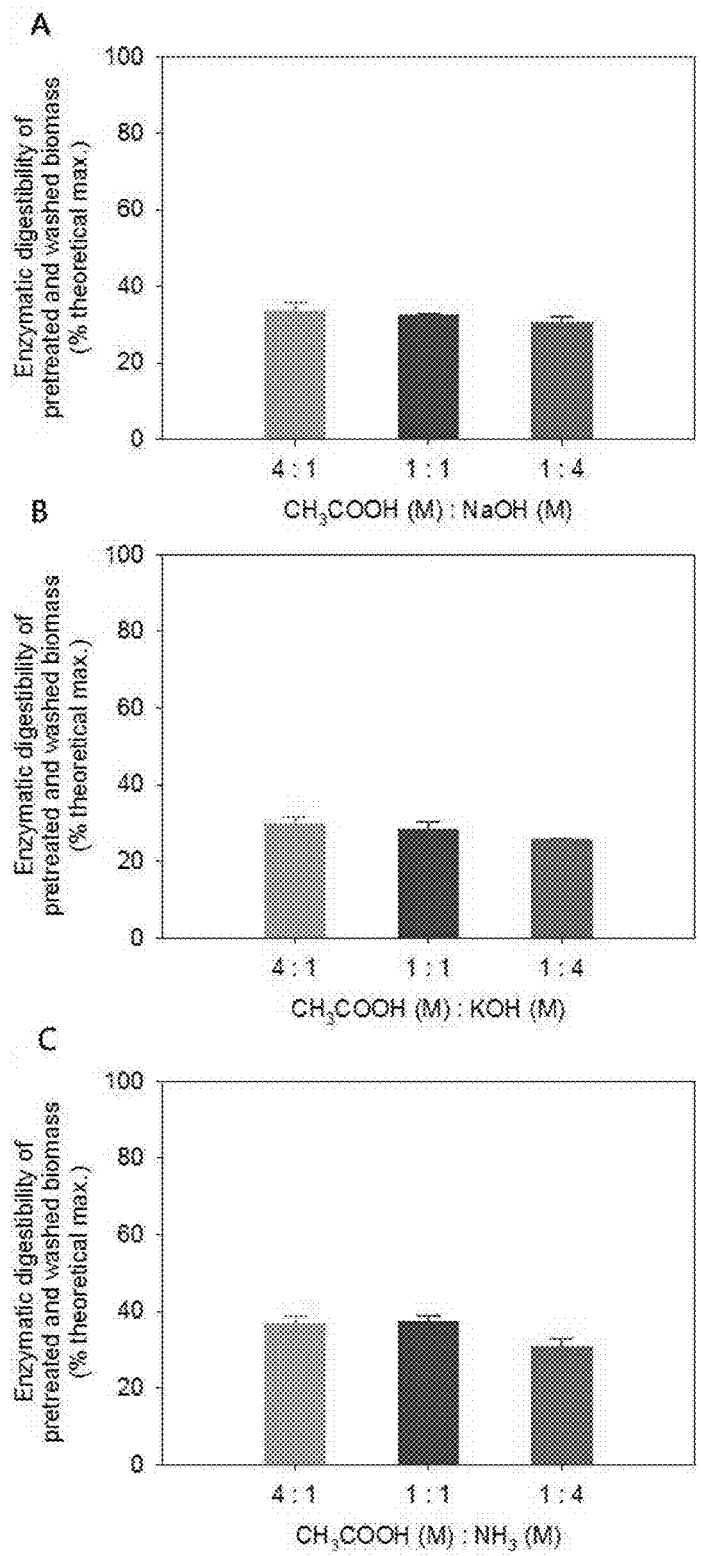
FIGS. 6A, 6B and 6C-FIG. 6A shows enzymatic digestibility obtained through enzymatic hydrolysis after pretreatment of rice straw with mixture catalyst of $CH_3COOH/NaOH$ at various mixing ratio.

FIGS. 4 to 6 show enzymatic digestibility obtained through enzymatic hydrolysis after pretreatment of rice straw with mixture catalysts obtained by varying a type and mixing ratio of an acid and a base, wherein the mixture catalyst was obtained by mixing a 0.05 M acid and a 0.05 M base at a molar ratio at 190° C., loading a 10% (w/v) substrate in the mixture catalyst in a mini thermal reactor, pretreating with reaction at 190° C. for 2 minutes, and then performing enzymatic hydrolysis using 15 FPU Accellerase 1000/g-glucan (while stirring at pH 4.8 at 50° C. at 200 rpm for 50 hours).

As a result, mixture catalysts of a strong acid and a strong base showed similar patterns based on a mixing ratio, and mixture catalysts of a weak acid and a strong base showed no significant difference in a saccharification yield under an acidic, neutral, basic condition, which indicates that there is the need for condition optimization.

Figures 7A, 7B, 7C:
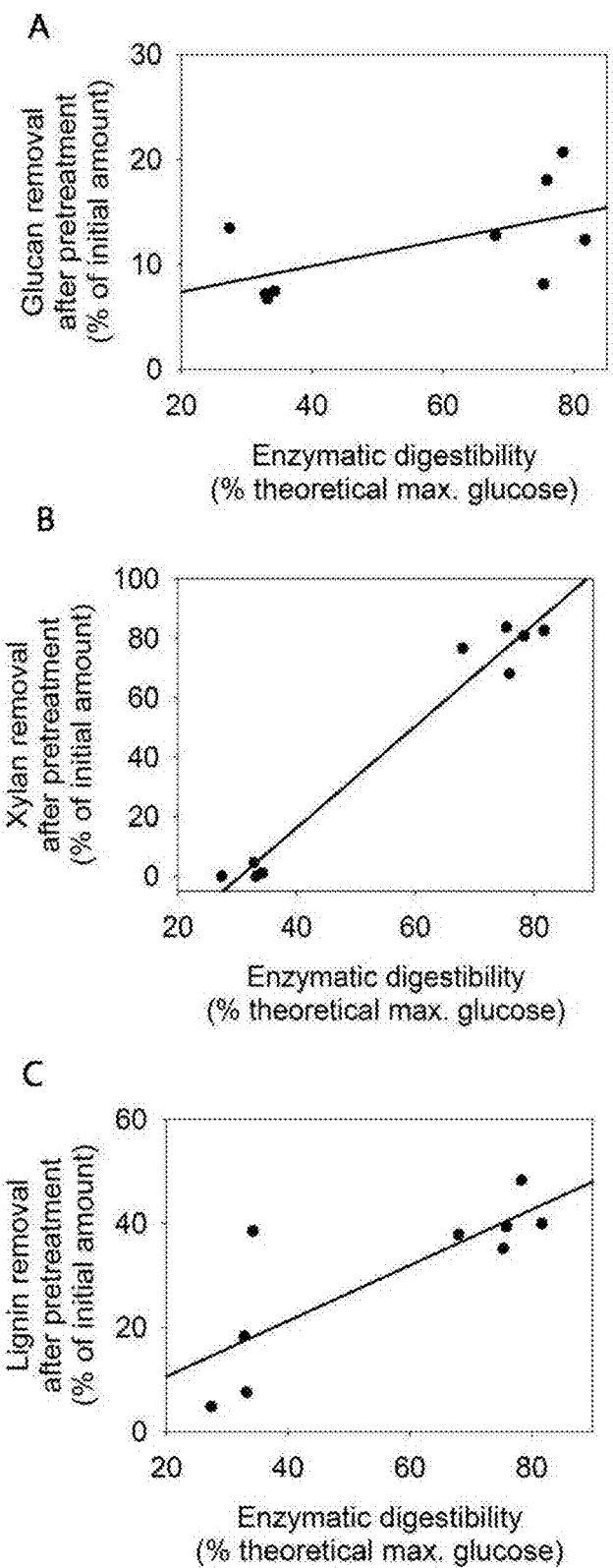
FIGS. 7A, 7B and 7C shows results of comparing a relationship with enzymatic digestibility in accordance with a change in constituent ingredients of rice straw such as glucan (FIG. 7A), xylan (FIG. 7B), and lignin (FIG. 7C) using an acid-base mixture catalyst of the present invention.

FIG. 7 shows results of comparing a relationship between data obtained through composition analysis after pretreatment with an acid-base mixture catalyst in an acidic range at 190° C. for 2 minutes and data obtained through hydrolysis while stirring at 50° C. at 200 rpm for 50 hours, wherein a correlation between glucan and a hydrolysis ratio was 0.20, a correlation between xylan and a hydrolysis ratio was 0.95, and a correlation between lignin and a hydrolysis ratio was 0.91, and therefore common effects of xylan removal as an effect of an acidic solution and lignin removal as an effect of a basic solution were observed.

Figure 8:
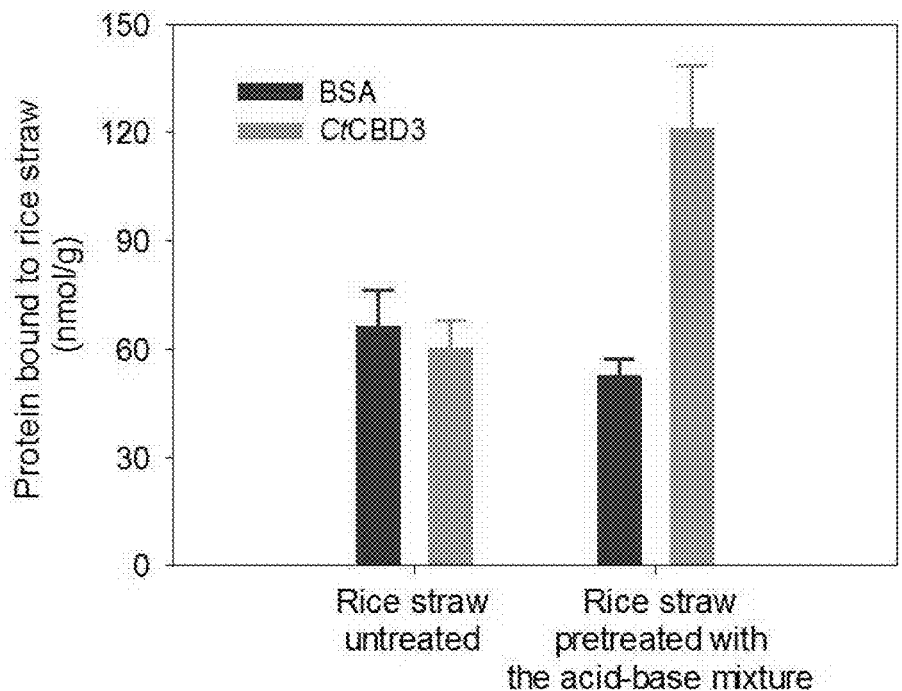
FIG. 8 shows a comparison between enzymatic accessibility of rice straw which is pretreated using an acid-base mixture catalyst of the present invention or not pretreated.

FIG. 8 shows a comparison of enzymatic accessibility of rice straw which is pretreated or not treated, wherein the binding reaction with rice straw was performed using BSA (control group) and CtCBD3 in a 50 mM phosphate buffer solution at pH 7 at 4° C. for 3.5 hours, and as a result, it was confirmed that accessibility with respect to cellulose is improved.

Figure 9:
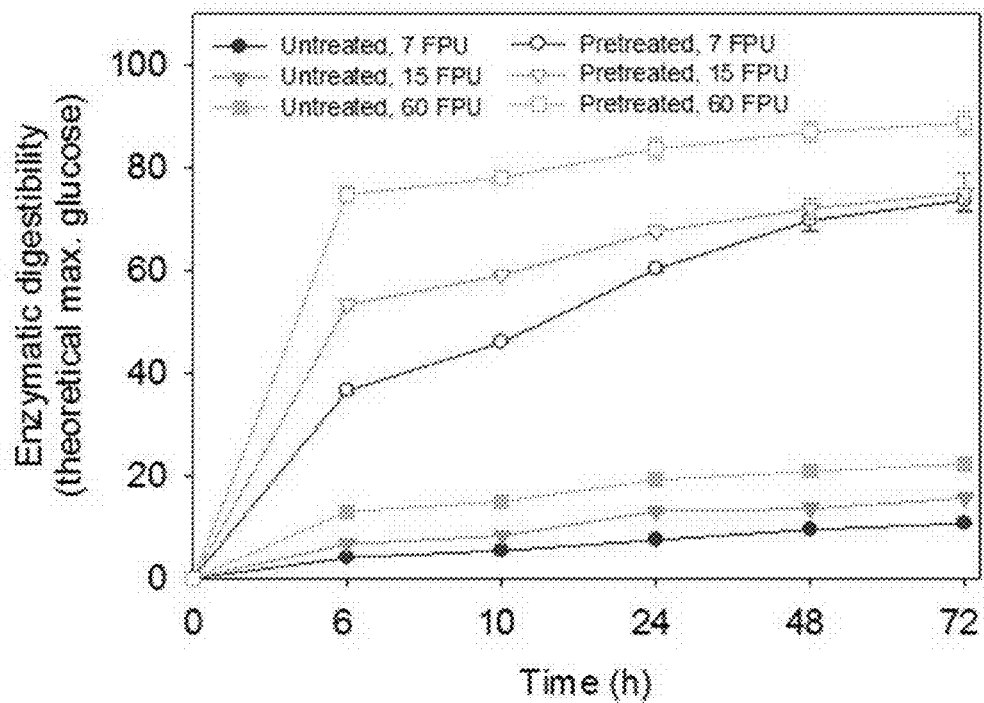
FIG. 9 shows effects of pretreatment of rice straw using an acid-base mixture catalyst on enzymatic saccharification of the present invention.

FIG. 9 shows effects of pretreatment with an acid-base mixture catalyst on enzymatic saccharification, wherein, when pretreatment was performed, a hydrolysis ratio at a concentration for treating cellulase was about 60 to about 80%, but in the case of biomass which was not pretreated, a hydrolysis ratio was 20% or less.

Figure 10:
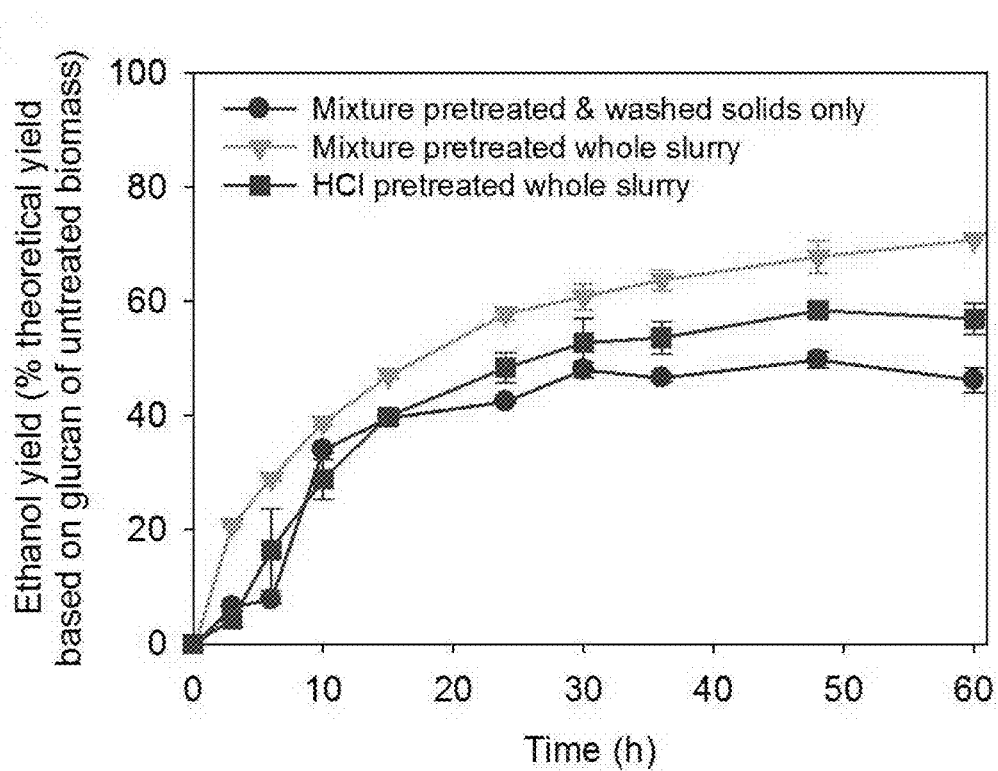
FIG. 10 shows the production yield of ethanol by simultaneous saccharification and fermentation of rice straw pretreated using an acid-base mixture catalyst of the present invention over time.

FIG. 10 shows results of measuring the production yield of ethanol by simultaneous saccharification and fermentation of pretreated biomass, wherein it can be seen that when a mixture catalyst of an acid and a base was used, ethanol yield is improved by as much as 17.5% than when biomass was pretreated with only an acid catalyst, and also the yield is improved by as much as about 20% than when a washing process was undergone after pretreatment with a mixture catalyst.

Figure 11:
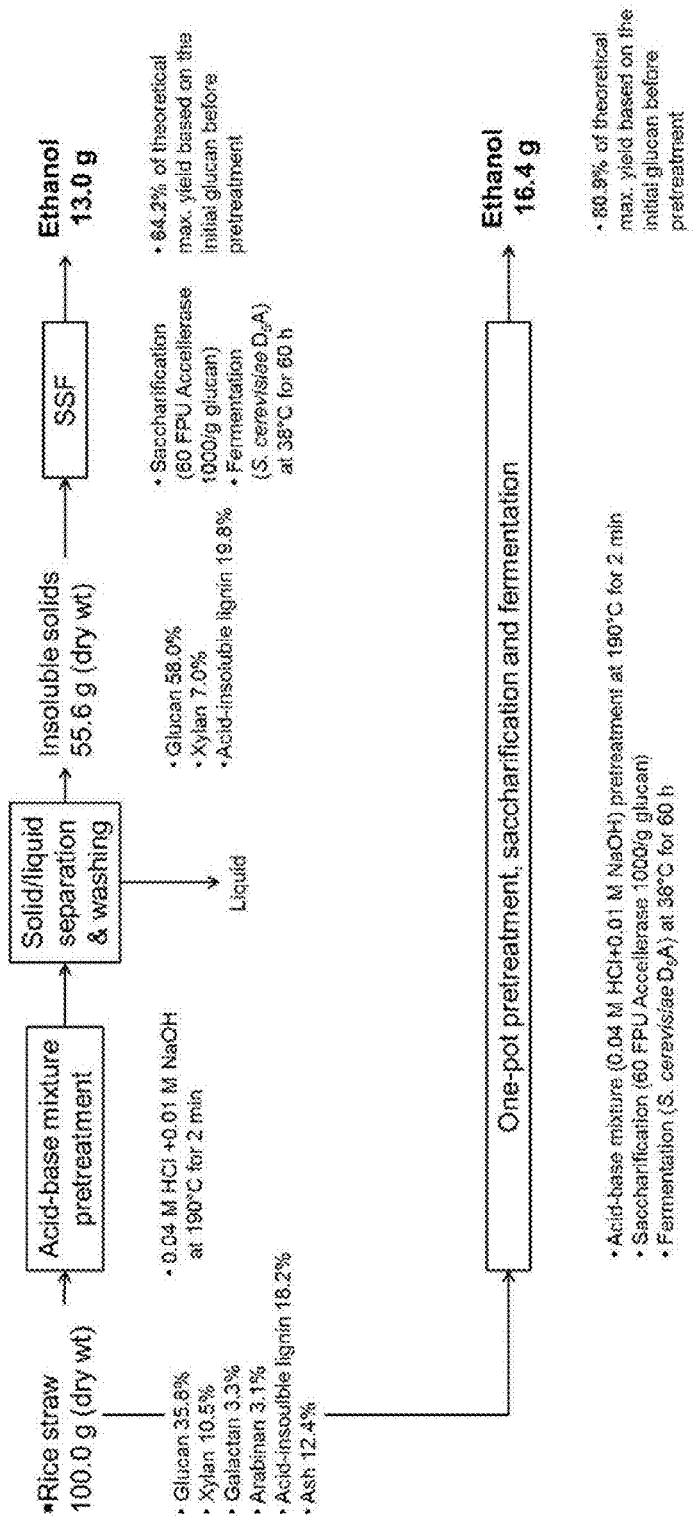
FIG. 11 is a schematic view illustrating a comparison of the mass yield of ethanol from rice straw in accordance with the overall process of the present invention.

Finally, it was found that an additional 3.4 g of ethanol were produced through process integration after pretreatment based on 100 g of biomass under the limitation that only glucose was used compared to when individual processes were performed separately (FIG. 11).

EXAMPLE 2

Investigation of Enzymatic Digestibility in Accordance with Pretreatment of Oil Palm Frond An oil palm frond was used as lignocellulose and was pretreated with an acid-base mixture catalyst, and then a saccharification yield was measured through enzymatic hydrolysis.

In order to confirm effects of pretreatment with an acid-base mixture catalyst, a mixture catalyst mixed based on types of an acid and a base was prepared, wherein a mixing ratio (a pH condition) and concentration of the mixture catalyst were optimized, and enzymatic digestibility was compared. Conditions of pretreatment and a method for performing enzymatic hydrolysis are the same as in Example 1.

An oil palm frond was harvested, washed, dried, and then cut into a range of 90 to 1000 μm using a high speed rotary cutter (MF 10 commercially available from IKA, Staufen, Germany).

Figure 12:
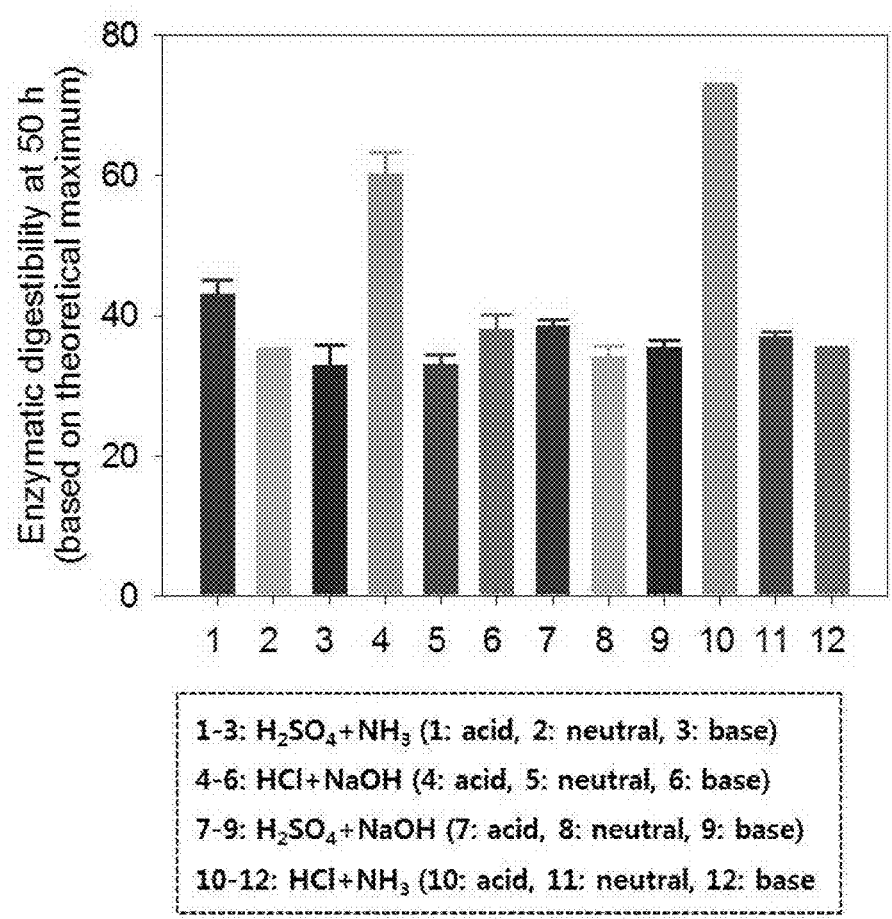
FIG. 12 shows effects of pretreatment of an oil palm frond under acidic, neutral, and basic conditions after the preparation of mixture catalysts based on types of an acid and a base.

FIG. 12 shows an obtained result of pretreatment effect of oil palm frond under acidic, neutral, and basic conditions after the preparation of mixture catalysts based on types of an acid and a base, wherein individual mixture catalysts show high enzymatic digestibility under an acidic condition, but in the case of sulfuric acid and sodium hydroxide or ammonia, the difference in a saccharification yield under acidic, neutral, and basic conditions was not significant. In this case, it seems that condition such as pretreatment conditions, a mixing concentration and the like need to be optimized.

Figure 13:
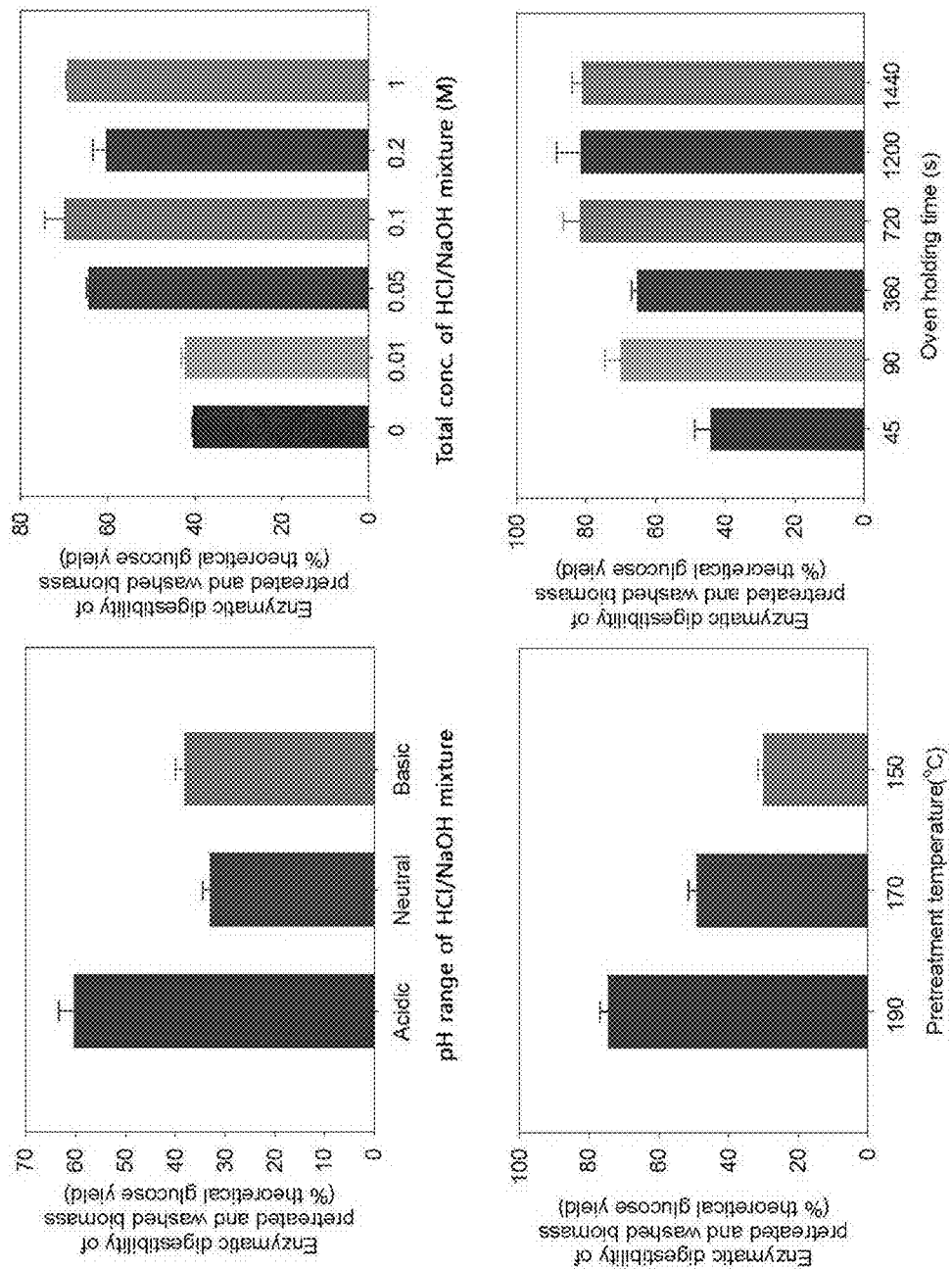
FIG. 13 shows enzymatic digestibility obtained by performing enzymatic hydrolysis on a whole slurry after the pretreatment of 10% (w/v) substrate based on a pH range, a total concentration of an acid-base mixture catalyst, a pretreatment temperature (150, 170, and 190° C.), and a pretreatment time (45, 90, 360, 720, 1200, and 1440 seconds) in a mini thermal reactor.

FIG. 13 shows enzymatic digestibility obtained by performing enzymatic hydrolysis on a whole slurry with the addition of 15 FPU/g glucan and stirring at pH 4.8 at 50° C. at 200 rpm for 50 hours after the preparation of a 10% (w/v) substrate based on a pH range and total concentration of an acid-base mixture catalyst, a pretreatment temperature (150, 170, and 190° C.), and a pretreatment time in a mini thermal reactor (45, 90, 360, 720, 1200, and 1440 seconds), wherein, as with the above-described rice straw, in the case of pretreatment with an acid-base mixture catalyst, the more a concentration of a mixture catalyst increased under an acidic condition, the higher effects of pretreatment were, and a pretreatment temperature was the most effective at 190° C. and effects were maintained when a reaction time is 90 seconds or more.

EXAMPLE 3

Investigation of Saccharification Yield in Accordance with Pretreatment of Sugarcane Bagasse Sugarcane bagasse was used as lignocellulose, was pretreated with an acid-base mixture catalyst, and then a saccharification yield was measured through enzymatic hydrolysis.

In the case of sugarcane bagasse, sugarcane was harvested, washed, dried, and then was cut into a range of 90 to 1000 μm using a high speed rotary cutter (MF 10 commercially available from IKA, Staufen, Germany).

In order to confirm effects of pretreatment with an acid-base mixture catalyst, a mixing molar ratio (12 to 2:1=acidic; 1:1=neutral; 1:2 to 4: basic condition) and concentrations of an acid and a base were optimized, and enzymatic digestibility was compared. Conditions of pretreatment and a method for performing enzymatic hydrolysis are the same as in Example 1.

FIG. 14 shows enzymatic digestibility of pretreated and washed sugarcane bagasse based on a total dry weight of untreated input biomass in accordance with a mixing molar ratio of an acid (HCl)-base (NaOH) mixture catalyst (a final concentration is 0.1 M) (A) and a concentration of an acid-base mixture catalyst (mixed at a molar ratio of an acid: a base=2:1) (B). Pretreatment was performed at 190° C. in conditions of ramping for 3 minutes and then holding for 2 minutes, and an amount of solids loading was 10% (w/v). Enzymatic hydrolysis was performed using 15 FPU of cellulase (Cellic CTec2)/g glucan at 50° C. (pH 4.8) at 200 rpm for 50 hours.

Figures 14A, 14B:
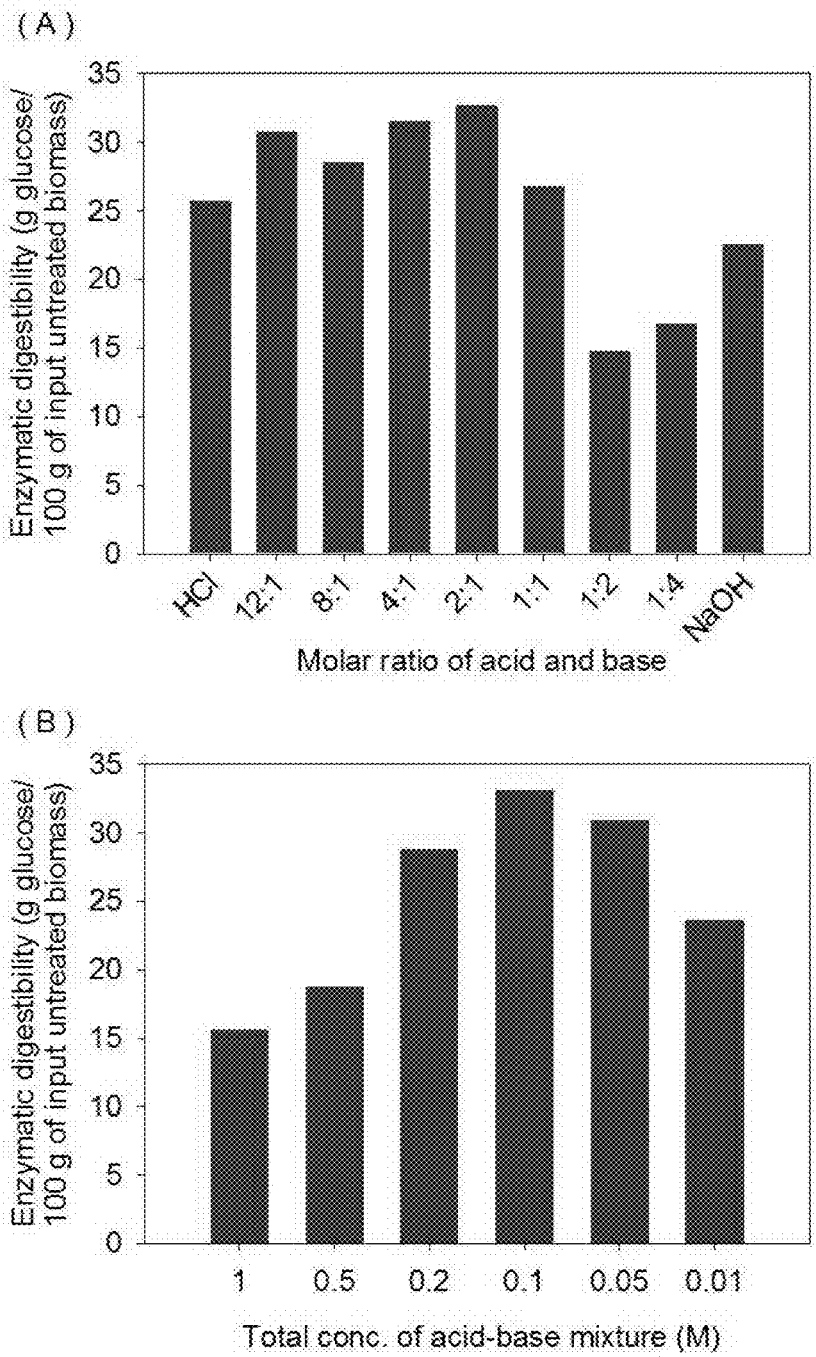
FIGS. 14A and 14B show enzymatic digestibility of pretreated sugarcane bagasse in accordance with a mixing molar ratio of an acid-base mixture catalyst of the present invention (a final concentration is 0.1 M) (FIG. 14A) and a concentration of an acid-base mixture catalyst (mixed at a molar ratio of an acid:a base=2: 1) FIG. 14(B).

As shown in FIG. 14, in the case of pretreatment with an acid-base mixture catalyst under an acidic condition, a superior saccharification yield was observed compared to neutral and basic conditions (FIG. 14A), it can be seen that a concentration of an acid-base mixture catalyst affects a saccharification yield.

Next, in order to confirm stability of an acid-base mixture catalyst at normal temperature, an acid-base mixture catalyst was incubated at normal temperature for a predetermined time before pretreatment, and then pretreatment of sugarcane bagasse and enzymatic hydrolysis were performed, and an insoluble solid recovery yield, a glucan recovery yield, a lignin removal rate, and enzymatic digestibility were measured in accordance with the incubation time of an acid-base mixture catalyst. Pretreatment was performed with a 0.1 M acid-base mixture catalyst (mix at a molar ratio of an acid: a base=2: 1) in a mini reactor at 190° C. in conditions of ramping for 3 minutes and then holding for 2 minutes, and an amount of solids loading was 10% (w/v). Enzymatic hydrolysis was performed using 15 FPU of cellulase (Cellic CTec2)/g glucan at 50° C. (pH 4.8) at 200 rpm for 50 hours.

Figures 15A, 15B, 15C, 15D:
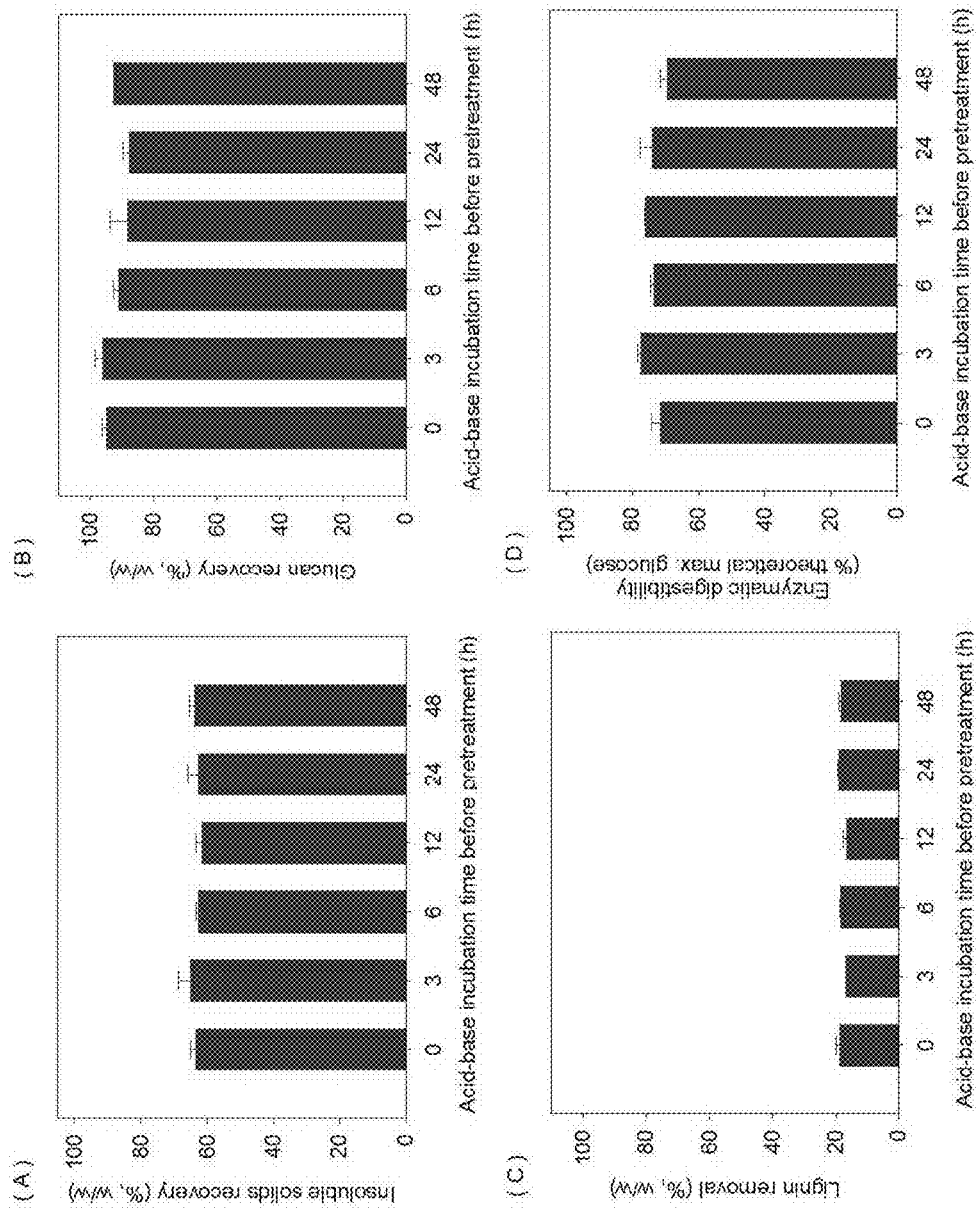
FIGS. 15A, 15B, 15C and 15D show an insoluble solids recovery yield (FIG. 15A), a glucan recovery yield (FIG. 15B), a lignin removal rate (FIG. 15C), enzymatic digestibility (FIG. 15D) of sugarcane bagasse obtained through pretreatment and enzymatic hydrolysis in accordance with the incubation time of an acid-base mixture catalyst of the present invention at normal temperature.

As shown in FIG. 15, catalytic activity for pretreatment was almost identical regardless of the incubation time of an acid-base mixture catalyst. Therefore, it can be seen that characteristics of an acid-base mixture catalyst as catalyst for pretreatment are maintained at normal temperature.

Figure 16:
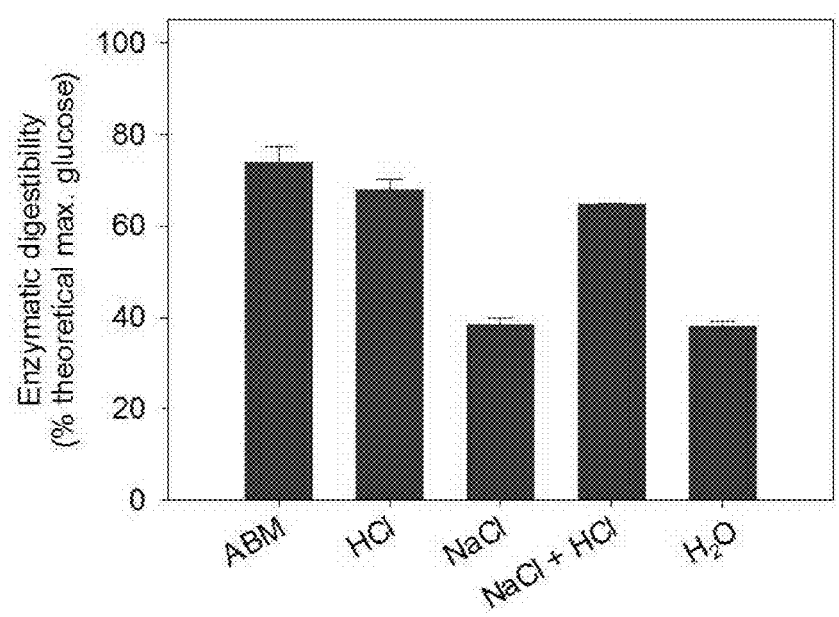
FIG. 16 shows enzymatic digestibility of sugarcane bagasse pretreated using an acid-base mixture catalyst, HCl, NaCl, a mixture catalyst of HCl+0.033 M NaCl, and water.

The following Table 2 shows results of composition analysis of sugarcane bagasse pretreated based on catalysts, wherein the acid-base mixture catalyst was similar to HCl and an HCl-NaCl mixture catalyst in terms of results of pretreatment, but a product pretreated with an acid-base mixture catalyst showed a relatively high saccharification yield (FIG. 16).

FIG. 16 shows enzymatic digestibility obtained through pretreatment of sugarcane bagasse by using an acid-base mixture catalyst of 0.067 M HCl+0.033 M NaOH, 0.033 M HCl, 0.033 M NaCl, an acid-base mixture catalyst of 0.033 M HCl+0.033 M NaCl, and water, wherein conditions of pretreatment and enzymatic hydrolysis is the same as described above.

TABLE 2

Composition analysis of sugarcane bagasse pretreated with different catalysts

| | untreated | acid-base mixture catalyst (0.067 M HCl ± 0.033 M NaOH) | HCl (0.033 M) | NaCl (0.033 M) | NaCl (0.033 M) ± HCl (0.033 M) | $H_2O$ |
|---|---|---|---|---|---|---|
| Component from insoluble solids (g per 100 g dry dried sugarcane bagasse before pretreatment) | | | | | | |
| insoluble solid recovery yield | NA$^d$ | 62.7 ± 3.2 | 62.2 ± 0.6 | 86.6 ± 2.9 | 63.6 ± 2.4 | 87.6 ± 2.5 |
| glucan | 40.9 ± 0.1 | 57.2 ± 1.6 | 57.8 ± 0.7 | 45.4 ± 1.9 | 58.5 ± 1.1 | 43.6 ± 1.2 |
| xylan | 26.5 ± 0.5 | — | — | 19.1 ± 0.8 | — | 19.6 ± 1.2 |
| other carbohydrates | 5.4 ± 0.1 | — | — | — | — | — |
| acid-insoluble lignin | 24.0 ± 0.1 | 19.4 ± 0.1 | 19.3 ± 0.1 | 21.1 ± 0.1 | 19.7 ± 0.3 | 20.6 ± 0.5 |
| acid-soluble lignin | 1.4 ± 0.1 | 1.3 ± 0.0 | 1.2 ± 0.0 | 1.4 ± 0.0 | 1.2 ± 0.0 | 1.4 ± 0.0 |

TABLE 2-continued

Composition analysis of sugarcane bagasse pretreated with different catalysts

| | untreated | acid-base mixture catalyst (0.067 M HCl ± 0.033 M NaOH) | HCl (0.033 M) | NaCl (0.033 M) | NaCl (0.033 M) ± HCl (0.033 M) | $H_2O$ |
|---|---|---|---|---|---|---|
| Component from dissolved solids (g per 100 g dry dried sugarcane bagasse before pretreatment) | | | | | | |
| glucose | NA[d] | 4.3 ± 0.0 | 3.1 ± 0.0 | 0.9 ± 0.0 | 3.8 ± 0.1 | 1.0 ± 0.0 |
| hemicellulose monomer[c] | NA[d] | 21.1 ± 0.3 | 18.4 ± 0.3 | 6.6 ± 0.2 | 21.4 ± 0.4 | 7.0 ± 0.3 |
| acetic acid | NA[d] | 2.8 ± 0.0 | 2.4 ± 0.0 | 0.1 ± 0.0 | 2.6 ± 0.0 | 0.1 ± 0.0 |
| formic acid | NA[d] | 0.2 ± 0.0 | 0.1 ± 0.0 | — | 0.2 ± 0.0 | — |
| furfural | NA[d] | 1.8 ± 0.1 | 1.3 ± 0.1 | 0.2 ± 00.0 | 1.4 ± 0.0 | 0.2 ± 0.0 |

[a]Pretreatment conditions: ramping at 190° C. for 3 minutes, holding for 2 minutes, and solids loading in an amount of 10% (w/v)
[b]Experimental data is represented as means ± standard deviations
[c]xylose, galactose, and mannose are included in a liquid fraction
[d]NA: untreated The present invention is a technique applicable to the field of bio-ethanol preparation.

What is claimed is:

1. A method for pretreating lignocellulosic biomass comprising:
    reacting an aqueous acid-base mixture catalyst having a pH value of 1 to 4 with lignocellulosic biomass at 100 to 200° C. for 60 seconds to 2 hours;
    wherein the acid is selected from the group consisting of sulfuric acid, maleic acid, hydrochloric acid, nitric acid, phosphoric acid, carbonic acid, formic acid, acetic acid, hydrofluoric acid, oxalic acid, citric acid, and mixtures of two or more thereof;
    wherein the base is selected from the group consisting of sodium hydroxide, potassium hydroxide, calcium hydroxide, barium hydroxide, ammonium hydroxide, calcium carbonate, potassium carbonate, ammonia, and mixtures of two or more thereof; and
    wherein said acid-base mixture catalyst has an acid:base molar ratio of 4:1, and has a total concentration of 0.05 M to 0.5 M.

2. The method for pretreating lignocellulo sic biomass according to claim 1, wherein the lignocellulosic biomass is mixed in a concentration of 4 g to 20 g per 100 mL of the acid-base mixture catalyst.

3. The method for pretreating lignocellulosic biomass according to claim 1, wherein the lignocellulosic biomass is selected from rice straw, giant miscanthus, sugarcane bagasse, corn byproducts, switchgrass, poplar, oil palm byproducts, or oak.

* * * * *